United States Patent
Charlton

(10) Patent No.: US 8,501,095 B2
(45) Date of Patent: *Aug. 6, 2013

(54) METHOD OF DISPENSING BIOSENSORS

(75) Inventor: Steven C. Charlton, Osceola, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 32 days.

This patent is subject to a terminal disclaimer.

(21) Appl. No.: 13/334,419

(22) Filed: Dec. 22, 2011

(65) Prior Publication Data

US 2012/0094319 A1    Apr. 19, 2012

Related U.S. Application Data

(60) Continuation of application No. 11/891,807, filed on Aug. 13, 2007, now Pat. No. 8,105,536, which is a division of application No. 10/382,786, filed on Mar. 7, 2003, now Pat. No. 7,270,247.

(60) Provisional application No. 60/364,848, filed on Mar. 18, 2002.

(51) Int. Cl.
*B65H 1/12*        (2006.01)

(52) U.S. Cl.
USPC .............. 422/68.1; 422/500; 221/22; 221/59

(58) Field of Classification Search
USPC ............... 422/500, 560, 561, 68.1, 430, 565, 422/566; 221/22, 59
See application file for complete search history.

(56) References Cited

U.S. PATENT DOCUMENTS

| | | | |
|---|---|---|---|
| 3,554,005 A | 1/1971 | Koblin et al. | |
| 3,728,081 A | 4/1973 | Bidanset | |
| 3,968,902 A | 7/1976 | Bachmann | |
| 4,142,863 A | 3/1979 | Covington et al. | |
| 4,374,529 A | 2/1983 | Kobayashi et al. | |
| 5,178,298 A | 1/1993 | Allina | |
| 5,575,403 A | 11/1996 | Miller et al. | |
| 5,609,823 A | 3/1997 | Harttig et al. | |
| 5,679,311 A | 10/1997 | Harttig et al. | |
| 5,757,666 A | 5/1998 | Schreiber et al. | |
| 6,065,660 A | 5/2000 | Cabrera | |
| 6,176,119 B1 | 1/2001 | Kintzig | |

FOREIGN PATENT DOCUMENTS

| | | |
|---|---|---|
| EP | 0 373 413 A1 | 6/1990 |
| EP | 0 373 629 A1 | 6/1990 |
| JP | 62 030962 A | 2/1987 |
| JP | 02-184761 A | 7/1990 |
| JP | 9 184819 A | 7/1997 |
| JP | 09-250998 A | 9/1997 |
| JP | 10-253570 A | 9/1998 |
| JP | 2001-141686 A | 5/2001 |
| JP | 2001-281199 A | 10/2001 |
| WO | WO 94/10558 A1 | 5/1994 |
| WO | WO 02/08753 A2 | 1/2002 |
| WO | WO 02/18940 A2 | 3/2002 |

*Primary Examiner* — In Suk Bullock
*Assistant Examiner* — Paul Hyun
(74) *Attorney, Agent, or Firm* — Nixon Peabody LLP

(57) ABSTRACT

A storage cartridge for dispensing biosensors used in the determination of an analyte in body fluid comprises a hollow body for housing a stack of biosensors having an open top, a flexible conveying member disposed over the open top of the body, the flexible conveying member having an aperture formed therein for receiving a biosensor from the stack of biosensors, a plate adapted to press the sliding conveying member against the open top to form a substantially moisture-impervious seal around the open top of the body and to permit the conveying member to slide between the plate and the open top, and a biasing mechanism the stack of biosensors towards the open top.

18 Claims, 6 Drawing Sheets

METHOD OF DISPENSING BIOSENSORS

CROSS-REFERENCE TO RELATED APPLICATIONS

This application is a continuation of Divisional U.S. patent application Ser. No. 11/891,807 filed Aug. 13, 2007, which issued as U.S. Pat. No. 8,105,536; U.S. patent application Ser. No. 11/891,807 is a divisional of U.S. patent application Ser. No. 10/382,786 filed Mar. 7, 2003, which issued as U.S. Pat. No. 7,270,247 on Sep. 18, 2007, and claims priority to Provisional Application No. 60/364,848 filed on Mar. 18, 2002, all of which are incorporated by reference in their entireties.

FIELD OF THE INVENTION

The present invention relates generally to blood glucose monitoring systems for determining the concentration of glucose in blood, and more particularly, to a storage cartridge for dispensing biosensors for use with blood glucose monitoring systems.

BACKGROUND OF THE INVENTION

It is often necessary to quickly obtain a sample of blood and perform an analysis of the blood sample. One example of a need for obtaining a sample of blood is in connection with a blood glucose monitoring system, which a user must frequently use to monitor the user's blood glucose level.

Those who have irregular blood glucose concentration levels are medically required to regularly self-monitor their blood glucose concentration level. An irregular blood glucose level can be brought on by a variety of reasons including illness such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky and confused. That person's judgment may become impaired and that person may eventually pass out. A person can also become very ill if their blood glucose level becomes too high—a condition known as hyperglycemia. Both conditions, hypoglycemia and hyperglycemia, are potentially life-threatening emergencies.

One method of monitoring a person's blood glucose level is with a portable, hand-held blood glucose testing device. The portable nature of these devices enables the users to conveniently test their blood glucose levels wherever the user may be. The glucose testing device includes a biosensor to harvest the blood for analysis. One type of biosensor is the electrochemical biosensor. The electrochemical biosensor includes a regent designed to react with glucose in the blood to create an oxidation current at electrodes disposed within the electrochemical biosensor which is directly promotional to the users blood glucose concentration. Such a biosensor is described in U.S. Pat. Nos. 5,120,420, 5,660,791, 5,759,364 and 5,798,031, each of which is incorporated herein in its entirety. Another type of sensor is an optical biosensor, which incorporates a reagent designed to produce a colorimetric reaction indicative of a user's blood glucose concentration level. The colorimetric reaction is then read by a spectrometer incorporated into the testing device. Such an optical biosensor is described in U.S. Pat. No. 5,194,393, which is incorporated herein by reference in its entirety.

In order to check a person's blood glucose level, a drop of blood is obtained from the person's fingertip using a lancing device, and the blood is harvested using the biosensor. The biosensor, which is inserted into a testing unit, is brought into contact with the blood drop. The biosensor draws the blood, via capillary action, inside the biosensor and the ensuing electrochemical reaction is measured by the test unit which then determines the concentration of glucose in the blood. Once the results of the test are displayed on a display of the test unit, the biosensor is discarded. Each new test requires a new biosensor.

Referring now to FIGS. 1 and 2, an example of a testing device 10 and a package 30 of biosensors 12 ("sensor pack") are shown, respectively. The sensor pack 30 is designed to be housed within the testing device 10. Prior to each test, a collection area 14 of an individual biosensor 12 is pushed by a mechanism within the testing device 10 through its packaging and is extended from the testing device 10 through a slot 16 for harvesting a sample of blood. The testing device 10 includes a slider 18 for advancing the test tensor 12. In FIG. 1, a biosensor 12 is shown extending from the testing device 10. The collection area 14 extends from the testing device 10, while a contact area, disposed at the opposite end of the biosensor 12 shown in FIGS. 1 and 2, remains inside the testing device 10. The contact area includes terminals that electrically couple the electrodes to a meter disposed within the testing device 10 for measuring the oxidation current produced at the electrodes by the reaction of glucose and the reagent. The test unit includes a display 20.

Referring now to FIG. 2, biosensors 12 are shown disposed in the sensor pack 30. The sensor pack 30 is made up of a circular disk 32 having ten individual compartments (blisters) 34 arranged radially. The disk is made from an aluminum foil/plastic laminate which is sealed to isolate the sensor from ambient humidity and from other sensors with a burst foil cover 36. Each biosensor 12 is kept dry by a desiccant located inside a desiccant compartment 37 disposed adjacent to the compartment 34.

To retrieve a sensor, a mechanism disposed within the testing device 10, such as a knife, is driven down through the burst foil into an individual elongated compartment 34 at the end closest to the hub of the disk 32 and then moved radially toward the perimeter of the blister 34. In doing so, the knife engages the contact area 38 (fish tail) of the sensor in that compartment. Radial travel of the knife pushes the tip of the sensor out through the burst foil 36 and through parts of the testing device 10 such that the collection area 14 of the sensor 12 is completely out of the testing device 10 and ready to receive a fluid test sample such as blood. For this stage, it is essential that the bond between the base and lid of the sensor withstand the sheer forces generated when the sensor bursts out through the foil 36. This method of providing a sensor ready for use is more fully described in U.S. Pat. No. 5,575,403, which is incorporated herein by reference in its entirety.

Further details of the operational and mechanical aspects of the testing device 10 and sensor pack 30 are more fully described in U.S. Pat. Nos. 5,575,403, 5,630,986, 5,738,244, 5,810,199, 5,854,074 and 5,856,195, each of which are hereby incorporated by reference in their entireties.

A drawback associated with this flat array of testing devices is the large area that is occupied. The size of testing devices that internally house such a flat array package constrains the size of the package (i.e., the number of sensors), thus making it difficult to increase the number of sensors per package. Accordingly, there exists a need for a testing system wherein the biosensor package size is independent of the testing device.

SUMMARY OF THE INVENTION

A storage cartridge for dispensing biosensors used in the determination of an analyte in body fluid comprises a hollow body for housing a stack of biosensors having an open top, a flexible conveying member disposed over the open top of the body, the flexible conveying member having an aperture formed therein for receiving a biosensor from the stack of biosensors, a plate adapted to press the sliding conveying member against the open top to form a substantially moisture-impervious seal around the open top of the body and to permit the conveying member to slide between the plate and the open top, and means for biasing the stack of biosensors towards the open top The above summary of the present invention is not intended to represent each embodiment, or every aspect, of the present invention. Additional features and benefits of the present invention will become apparent from the detailed description, figures, and claims set forth below.

Figure 1:
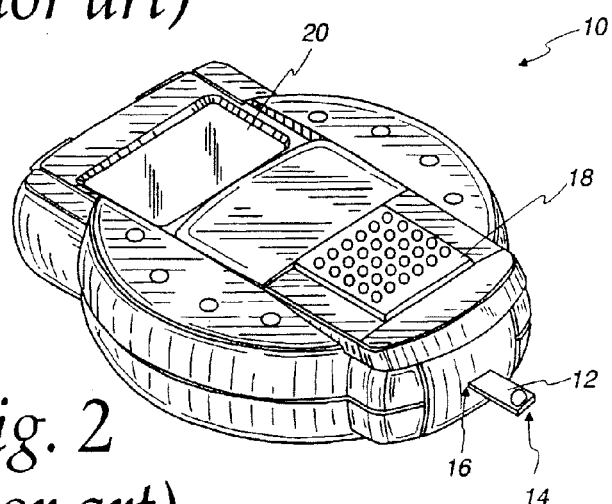
FIG. 1 is a perspective view of a prior art testing device.

While the invention is susceptible to various modifications and alternative forms, specific embodiments will be shown by way of example in the drawings and will be desired in detail herein. It should be understood, however, that the invention is not intended to be limited to the particular forms disclosed. Rather, the invention is to cover all modifications, equivalents and alternatives falling within the spirit and scope of the invention as defined by the appended claims.

DETAILED DESCRIPTION OF THE ILLUSTRATED EMBODIMENTS

Figure 2:
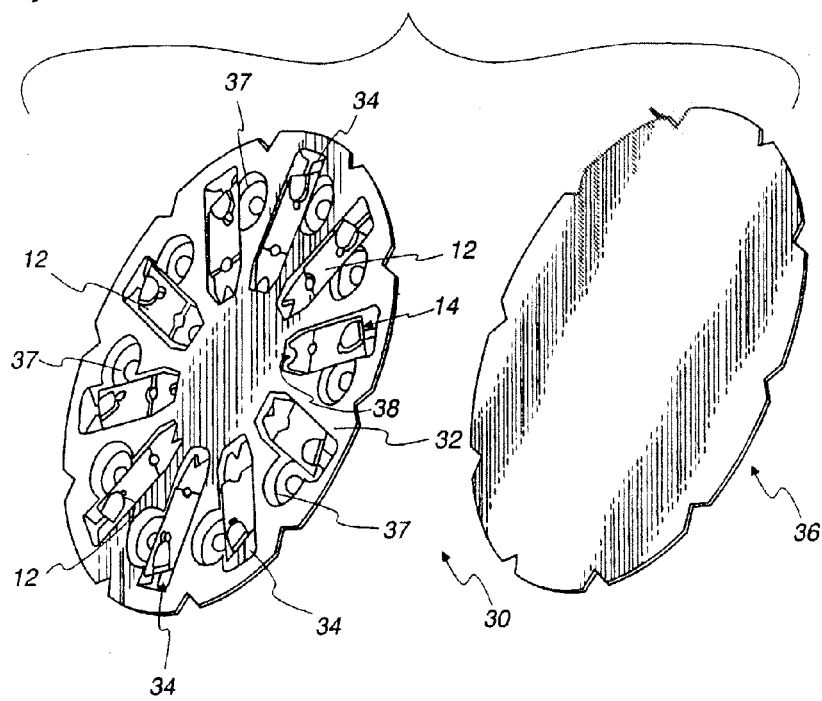
FIG. 2 is a perspective view of a prior art sensor pack having a foil lid removed.
Figure 3:
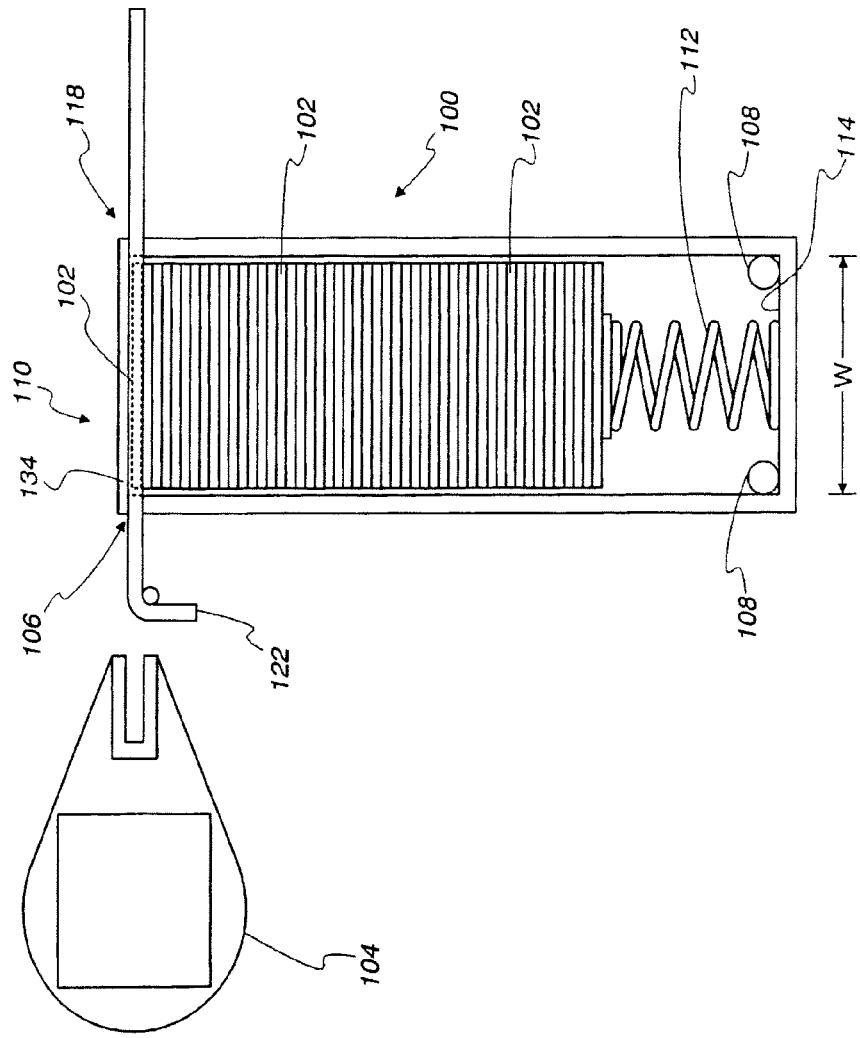
FIG. 3 is a first side view of a storage cartridge for biosensors according to one embodiment of the present invention.

Referring now to FIG. 3, there is shown a sensor cartridge 100 for storing a plurality of biosensors 102, such as the biosensors 12 described in connection with FIGS. 1 and 2, according to one embodiment of the present invention. Also shown in FIG. 3 is a testing device 104 which receives a biosensor 102 from the sensor cartridge 100 for determining a person's blood glucose level. The testing device 104 functions similar to that of the prior art testing device 10 shown in FIG. 1. The storage cartridge 100 provides a sealed, substantially moisture-impervious environment for storing the plurality of biosensors 102. According to one embodiment of the storage cartridge 100, the plurality of biosensors 102 are stacked, substantially one on top of the next, as shown in FIGS. 3-6. Generally, in use, the biosensors 102 are dispensed from the storage cartridge 100 via a sealed outlet 106.

The stacked biosensors 102 are in vapor communication with a desiccant material 108 disposed within the storage cartridge 100. The desiccant material 108 maintains the interior of the sensor cartridge 100 at an appropriate humidity level so that the reagent material disposed within the biosensors 102 is not adversely affected prior to being used. The desiccant material 108 is in the form of a small bag, round bead of material, a hot melt, a molded shape or any other form that can be readily disposed in the sensor cartridge 100. While the desiccant material 108 shown (FIG. 3) is disposed towards the bottom of the storage cartridge 102, the desiccant material 108 may be disposed anywhere practical within the storage cartridge 100 according to alternative embodiments of the storage cartridge 100. The amount of such desiccant material 108 placed within the sensor cartridge 100 will be dependent on the amount that is required to maintain the interior of the sensor cartridge 100 in a desiccated state. One type of commercially available desiccant material that can be used in one embodiment of the present invention is 13× synthetic molecular sieves from Multisorb Technologies Inc. of Buffalo, N.Y., available in powder, pellet and bead forms.

The sensor cartridge 100 is made of a rigid, moisture-impervious material such as plastic. Each of the biosensors are approximately 0.50 inch long (about 12.70 mm), approximately 0.03 inch thick (about 0.76 mm) and approximately 0.20 inch wide (about 5.08 mm). The interior of the of the sensor cartridge 100 is dimensioned only slightly larger than the length and width of the biosensors 120 to allow the biosensors 102 to move vertically within the storage cartridge (as described below) but not side-to-side (as viewed in FIG. 3) so that the stack of the biosensors 102 is maintained. For example, according to one embodiment of the storage cartridge 100, the storage cartridge 100 has an interior width W of approximately 0.52 inch (about 13.21 mm) and an interior depth (into the page as viewed in FIG. 3) of approximately 0.22 inch (about 5.59 mm). The interior height H is approximately 2.25 inch (about 57.15 mm) for an embodiment of the storage cartridge that is adapted to houses approximately fifty sensors. The interior height H can be varied according to alternative embodiments of the storage cartridge 100 to accommodate an increased or decreased number of bio sensor 102.

The sensors 102 are dispensed from the storage cartridge 100 via the sealed outlet 106 located towards the top 110 of the storage cartridge. The stack of biosensors 102 is biased upward towards the top 110 of the storage cartridge 100 by a resilient member such as a spring 112 disposed between the stack of biosensors 102 and an interior bottom surface 114 of the storage cartridge 100.

Figure 4:
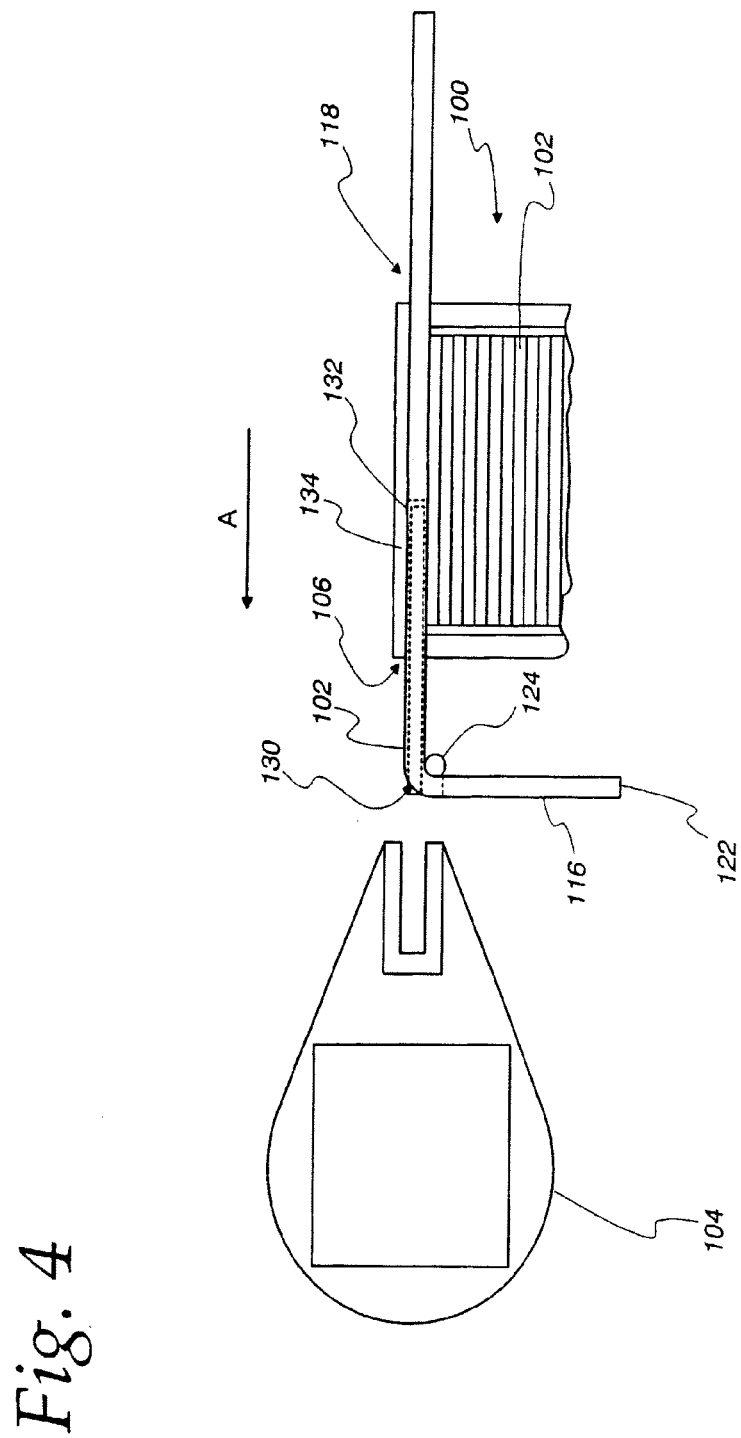
FIG. 4 is a second side view of a storage cartridge for biosensors according to one embodiment of the present invention.
Figure 7:
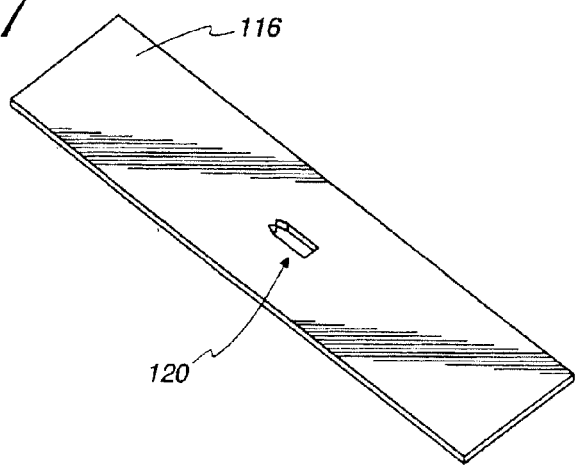
FIG. 7 is a perspective view of a flexible sliding conveying member for the storage cartridge for biosensors shown in FIGS. 3-6.

Referring now also to FIG. 4, the top of the storage cartridge 100 is sealed by a flexible, slideable conveying member 116 that is pressed against the top 110 of the storage cartridge 100 by a top plate 134. According to one embodiment, the conveying member 116 is made out of polyolefin, which includes the attributes of low moisture vapor transmission, flexibility and a lubricious surface. According to one embodiment, the conveying member 116 protrudes from the storage cartridge 100 at the outlet 106 as well as through a second outlet 118 located on the opposite side of the storage cartridge 100. The conveying member 116 seals outlets 106, 118 as described below. The conveying member 116 (FIG. 7) includes a cutout or nest 120. The nest 120 is designed to fit around a biosensor 102. Put another way, the nest 102 receives the biosensor 102. As described in further detail below, the conveying member 116, which surrounds a biosensor 102, is pulled across the top of the storage cartridge 100 (from right to left as viewed in FIG. 3) and, in turn, the biosensor 102 is pulled/dragged from the storage cartridge 100. As shown in FIG. 7, the nest 120 is cut in the shape of a biosensor such as the biosensors 12 depicted in FIG. 2. In other embodiments, the nest 120 is more general in shape (e.g., a rectangle) to accommodate biosensors of a variety of shapes.

In operation, the user of the storage cartridge 100 and testing device 104 pulls a first end 122 of the conveying member 116. Either prior to the user's pulling or during, the spring 112, which constantly biases the stack of biosensors 102 upward, pushes the biosensor 102 at the top of the stack into the nest 120. This biosensor 102, within the nest 120 and surrounded by the conveying member 116, is pulled along with the conveying member 116 towards the outlet 106. The flexible conveying member 116 is pulled around a post 124 at an approximately 90° angle. In FIGS. 3-6, the post 124 is shown disposed away from the storage cartridge 100. However, in other embodiments, the post 124 is an integral component of the storage cartridge 100 as is shown in FIG. 6. Alternatively still, the post 124 may comprise a rounded corner of the storage cartridge 100.

Referring now to FIG. 4, the conveying member 116 is pulled in the direction indicated by arrow A from the storage cartridge 100 such that the biosensor 102 is partially protruding from the outlet 106 of the storage cartridge 100. A leading end 130 of the biosensor 102, surrounded by the conveying member 116, is proximate the post 124. As the flexible conveying member 116 is pulled around the post 124, the relatively rigid biosensor 102 continues to travel in a straight line (in the direction of arrow A). A trailing end 132 of the biosensor 102, which is still within the storage cartridge 100, is still constrained to its original path by the top plate 134 of the storage cartridge 100 and the adjacent lower biosensor 102.

Figure 5:
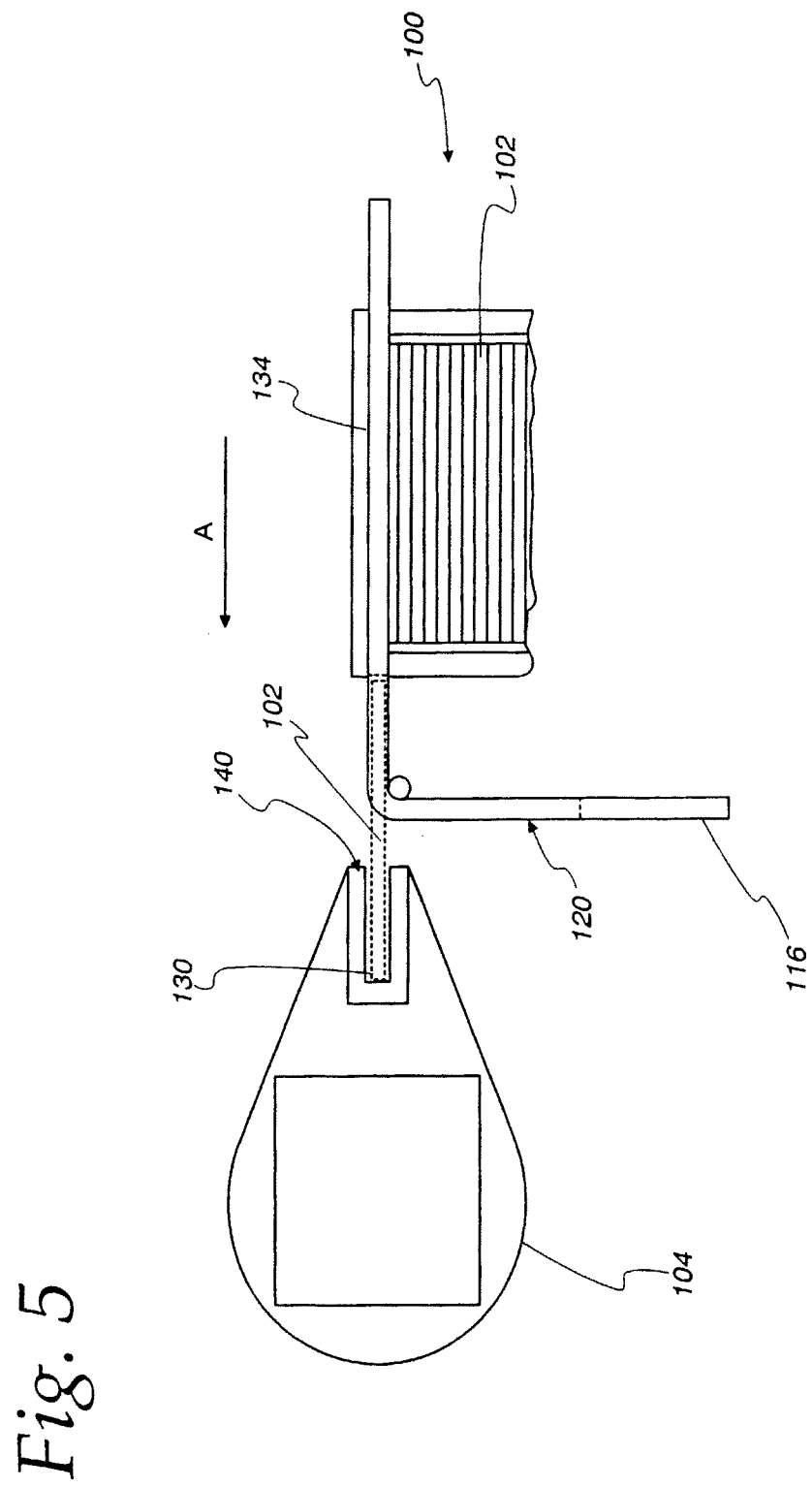
FIG. 5 is a third side view of a storage cartridge for biosensors according to one embodiment of the present invention.
Figure 6:
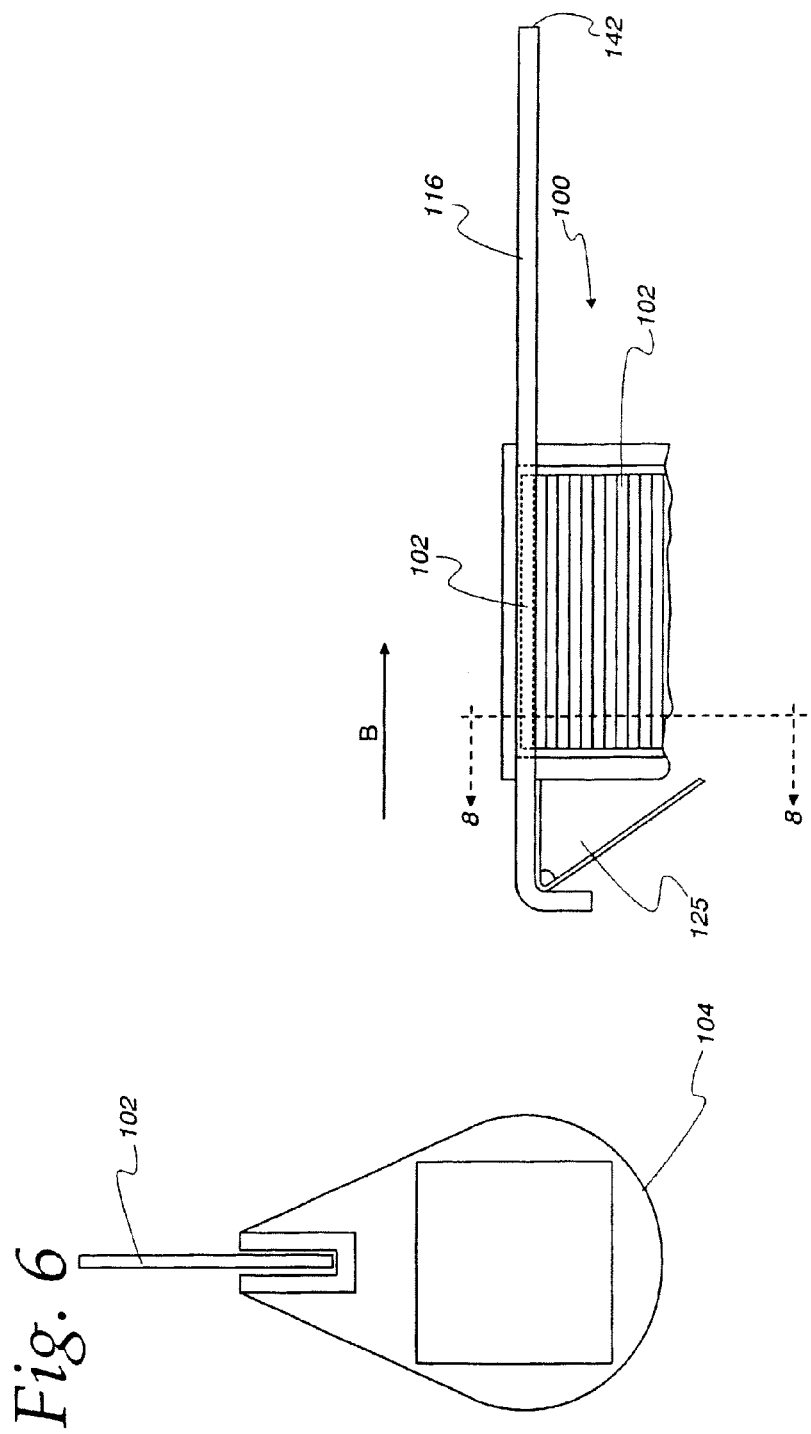
FIG. 6 is fourth side view of a storage cartridge for biosensors according to one embodiment of the present invention.

Referring now to FIG. 5, the conveying member 116 is pulled in the direction indicated by arrow A until a substantial portion of the leading end 130 of the biosensor 102 is extended beyond the post 124 and is not surrounded by the conveying member 116. The leading end 130 of the biosensor 102 is then forced into a mating portion 140 of the testing device 104. As the biosensor 102 is pulled out of the storage cartridge, the spring 112 forces a biosensor 102 within the storage cartridge upward against the conveying member 116.

Referring now also to FIG. 6, the biosensor 102 is now disposed within the testing device and can be used in the analysis of a sample of blood. The second end 142 of the conveying member 116 is pulled back in the direction indicated by arrow B causing the nest 120 to be brought back inside the storage cartridge 100 to receive another biosensor 102 for the next test. As the conveying member 116 is pulled back into the test cartridge 100 and the nest 120 passes over the stack of biosensors 102, the uppermost biosensor 102 is forced upward into the nest 120 by the spring 112.

In FIGS. 3-5 the post has 124 been shown as not attached to the storage cartridge 100. In FIG. 6, the post 124 is shown as a rounded corner of protrusion 125 which extends outward from the cartridge 100. In other alternative embodiments of the storage cassette 100, there is no protrusion 125 (or post 124) and the conveying member is simply pulled around the corner at the outlet 106 of the storage cartridge.

Figure 8A:
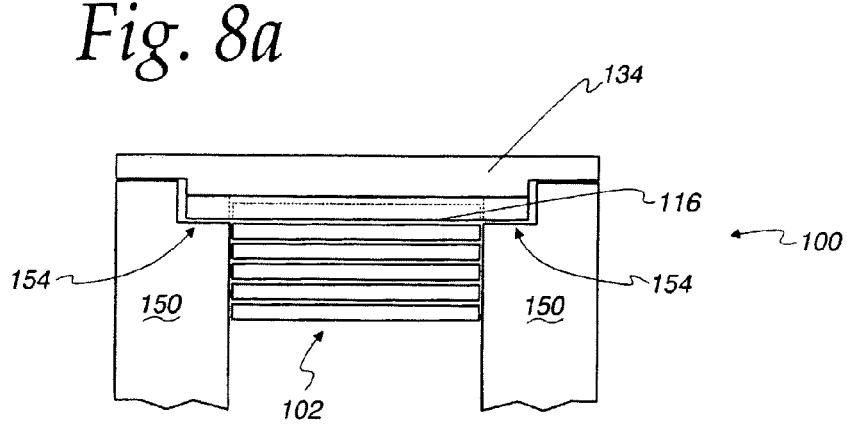
FIG. 8a is a cut-away view of the storage cartridge shown in FIG. 6 along dashed line 8.

Referring now to FIG. 8a there is shown a cut-away view of the storage cartridge 100 along dashed line 8 (FIG. 6). The conveying member 116 is disposed between side-walls 150 of the storage cartridge 100 and the top plate 134. The plate 134 functions as the top of the storage cartridge 100. The plate 134 is pressed down onto the conveying member 116 with sufficient pressure that a substantially moisture-impervious seal is formed between the top plate 134, the sliding conveying member 116 and the walls 150 of the storage cartridge. According to one embodiment, the pressed thickness of the conveying member 116 is at least slightly less than that of the biosensor 102 to facilitate the trapping and dragging of just one biosensor out of the storage cartridge. According to one embodiment of the present invention, a substantially constant amount of pressure is applied by the plate 134 to the conveying member 116 and the walls 150. A suitable fastener (e.g., screws, rivets, clamps) can be used to press the plate 134 against the conveying member 116 and walls 150 as described. However, the constant pressure applied to the conveying member 116 by the plate 134 should not be so great as to unduly inhibit the sliding of conveying member 116 when pulled by a user when dispensing of a biosensor 102. Constructing the conveying member 116 out of a lubricious material such as polyolefin, according to one embodiment, facilitates the sliding movement of the conveying member 116.

In an alternative embodiment of the storage cassette 110, the pressure applied to the conveying member 116 and walls 150 by the plate 134 may be temporarily reduced or eliminated during the dragging process. In such an embodiment, the reduced pressure may break the substantially moisture-impervious seal of the storage cassette 100. However, any moisture leaking into the storage cassette 100 during the temporary break in the seal is absorbed by the desiccant 108 (FIG. 3). A variety of mechanical schemes can be employed for varying the pressure applied by the top plate 134 according to alternative embodiments of the present invention. For example, in one embodiment, an adjustable clamp (not shown) may be used to vary the pressure applied by the top plate 134. In another embodiment, screws (not shown), such screws having heads large enough to be grasped by a user's fingers, may be used to vary the pressure applied by the top plate 134. Alternatively still, an elastic member (not shown) may apply sufficient pressure to the top plate 134 for forming the seal around the walls 150, but be elastic enough to allow the plate to lift slightly during the dragging process when a biosensor is being dispensed. In yet another alternative embodiment, a wedge-type of arrangement can be employed wherein the top plate 134 is inserted into grooves (not shown) disposed within the interior of walls 150 wherein the grooves direct the top plate 134 down into pressed contact with the conveying member 116.

Figure 8B:
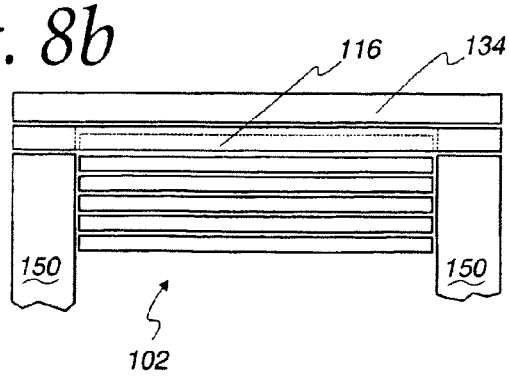
FIG. 8b is a cut-away view along dashed line 8 of FIG. 6 of an alternative embodiment of the storage cartridge.

As shown in FIG. 8a, according to one embodiment, the conveying member 116 is disposed on flat surfaces 154 which are integrally formed in walls 150. However, other configurations are possible according to various other alternative embodiments of the storage cassette 100. For example, the conveying member 116 is disposed directly on top of walls 150 according to the alternative embodiment of the storage cartridge 100 shown in FIG. 8b.

According to one embodiment of the storage cartridge 100, the biosensors 102 are arranged within the storage cartridge such that the leading end 130 of the biosensor 102 (i.e., the end of the first pulled from the cartridge 100) is the contact area of an electrochemical biosensor. As discussed in the background section, the contact area of the biosensor 102 includes terminals which electrically couple the biosensor 102 to the testing device 104. Dispensing the biosensors 102 in this manner is advantageous over many prior art biosensor dispensing schemes because the sample collection area (i.e., disposed on the end opposite the contact area in FIGS. 1 and 2) of the biosensor 102 never contacts or passes through the testing device 104. This arrangement removes the potential risk of cross-contamination in situations where the testing device 104 may be used by more than one patient.

According to still another alternative embodiment, the storage cartridge is part of the testing device. In such an embodiment, the portion of the testing device that receives the sensor is movable with respect to the storage cartridge such that the sample collection area of the sensor is available to receive the sample.

Referring back to FIG. 6, the second end 142 of the conveying member 116 has been shown and described as extending out of the storage cartridge through the second outlet 118. However, in alternative embodiments of the storage cartridge, the second end 142 of the conveying member 118 remains within the storage cartridge 100. According to one such embodiment, the second end is attached to a resilient member within the storage cartridge 100 for retracting the sliding conveying member 116 after a biosensor 102 has been dispensed. According to another such embodiment, the conveying member 116 is pushed back through the first outlet 106 by the user. According to yet another such embodiment, a mechanical apparatus such as a roller is integrated into the storage cartridge 100 for pushing or pulling the conveying member 116 back into the storage cartridge 100.

According to still another alternative embodiment of the storage cartridge 100 implements a length of conveying member 116 having a plurality of evenly spaced-apart nests 120 formed therein. The length of conveying member 116 is stored in the form of a roll, or is folded. After a portion of the conveying member 116 is pulled from the cartridge 100 and a sensor 102 is dispensed, that portion of the conveying member 116 can be torn or cut and discarded leaving a sufficient amount of conveying member to grasp for dispensing the next cartridge.

According to other alternative embodiments of the present invention, other biasing members are used in place of a resilient member (e.g. the spring 112 shown in FIG. 3) for upwardly (as view in FIG. 3) the stack of biosensors 102. For example, in such alternative embodiments, the biasing member may include a first magnet disposed on the interior bottom surface 114 of the storage cartridge 100 and a second repulsively disposed magnet attached to the stack of biosensors 102. The stack of sensors 102 is biased upward via electromagnetic forces that cause the first magnet and the second magnet to repulse (i.e., push away from) each other. In another alternative embodiment, the magnets comprise opposing ferromagnets as opposed to eletromagnets. Alternatively, a combination of electomagnets and ferromagnets may be used.

In other alternative embodiments, the biasing member may comprise a pneumatic system wherein a compressed gas is used to upwardly bias the stack of biosensors 102. According to one alternative embodiment, the stack of bio sensors 102 are disposed on the top-side of a piston in a piston-cylinder arrangement, wherein the cartridge 100 severs as the cylinder. A compressed gas disposed in the cylinder, beneath the piston, biases the stack of test sensors 102 towards the top 110 of the cartridge 100.

While the invention is susceptible to various modifications and alternative forms, specific embodiments thereof have been shown by way of example in the drawings and herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

What is claimed is:

1. A method for dispensing a biosensor used in the determination of an analyte in body fluid from a biosensor storage cartridge, the method comprising:
    providing a plurality of stacked biosensors within a hollow body of the storage cartridge, the hollow body being closed at a first end and open at a second end;
    disposing a flexible conveying member over the open second end, the conveying member forming at least one aperture therein;
    forming a seal over the open second end via the flexible conveying member;
    receiving a biosensor from the stack of biosensors in the at least one aperture formed in the conveying member; and
    actuating the conveying member such that the biosensor received in the at least one aperture is positioned for removal from the storage cartridge, the flexible conveying member being sufficiently flexible to assist in removing the biosensor therefrom.

2. The method of claim 1 further including biasing the stacked biosensors within the cartridge towards the sealed second end.

3. The method of claim 1 wherein the biasing includes a resilient member disposed between the stacked biosensors and the first end of the hollow body.

4. The method of claim 1 wherein the conveying member comprises polyolefin.

5. The method of claim 1 wherein the conveying member is made out of a material having a lubricious surface.

6. The method of claim 1 wherein the flexible conveying member has a low moisture vapor transmission rate.

7. The method of claim 1 wherein a portion of the flexible conveying member remains outside of the cartridge.

8. The method of claim 1 wherein each of the biosensors has a contact area for interfacing with a testing unit and a collection area for receiving the body fluid, the method further comprising stacking the biosensors within the hollow body such that each biosensor is dispensed contact area first.

9. The method of claim 1 further comprising measuring a reaction between a reagent disposed in the biosensor and the analyte in the received body fluid.

10. The method of claim 9 further comprising determining the concentration of the analyte in the body fluid.

11. A method for dispensing a biosensor used in the determination of an analyte in body fluid from a biosensor storage cartridge, the method comprising:
    providing a plurality of stacked biosensors within a hollow body of the storage cartridge, the hollow body being closed at a first end, open at a second end and having two sides;
    disposing a flexible conveying member over the open second end and generally within the sides of the hollow body, the conveying member forming at least one aperture therein;
    forming a substantially moisture-impervious seal over the open second end via the flexible conveying member;
    biasing the biosensors stacked within the cartridge towards the sealed second end;
    receiving a biosensor from the stack of biosensors in the at least one aperture formed in the conveying member; and
    actuating the conveying member such that the biosensor received in the at least one aperture is positioned for removal from the storage cartridge.

12. The method of claim 11 wherein the seal is formed by applying pressure to the conveying member.

13. The method of claim 11 further including removing the biosensor from the flexible conveying member, the flexible conveying member being sufficiently flexible to assist in removing the biosensor therefrom.

14. The method of claim 11 wherein the conveying member comprises polyolefin.

15. The method of claim 11 wherein a portion of the flexible conveying member remains outside of the cartridge.

16. The method of claim 11 wherein each of the biosensors has a contact area for interfacing with a testing unit and a collection area for receiving the body fluid, the method further comprising stacking the biosensors within the hollow body such that each biosensor is dispensed contact area first.

17. The method of claim 11 further comprising measuring a reaction between a reagent disposed in the biosensor and the analyte in the received body fluid.

18. The method of claim 17 further comprising determining the concentration of the analyte in the body fluid.

* * * * *